United States Patent [19]
Schmid

[11] 4,448,199
[45] May 15, 1984

[54] ELECTRODE FOR DETECTING BIOELECTRICAL SIGNALS

[76] Inventor: Walter Schmid, Fuchsweg 9, D-7911 Pfaffenhofen, München, Fed. Rep. of Germany

[21] Appl. No.: 351,870

[22] Filed: Feb. 24, 1982

Related U.S. Application Data

[63] Continuation-in-part of Ser. No. 142,741, Apr. 22, 1980, Pat. No. 4,375,219.

[30] Foreign Application Priority Data

Feb. 5, 1980 [DE] Fed. Rep. of Germany ....... 3004126

[51] Int. Cl.³ ............................................... A61B 5/04
[52] U.S. Cl. .................................... 128/639; 128/644
[58] Field of Search ............................... 128/639–641, 128/643, 644, 690, 798, 802, 803

[56] References Cited

U.S. PATENT DOCUMENTS 2,815,749  12/1957  Friedman ........................... 128/644

FOREIGN PATENT DOCUMENTS 2742058  3/1979  Fed. Rep. of Germany ...... 128/643
 55-2416  1/1980  Japan .................................. 128/639
55-70239  5/1980  Japan .................................. 128/639
 639525  2/1979  U.S.S.R. ............................. 128/639

OTHER PUBLICATIONS

De Luca et al., "Pasteless Electrode for Clinical Use", *Med. & Biol. Eng. & Comp.*, 1979, 17, 387–390.
Griffith et al., "Improved Capacitive ECG Electrodes . . .", *Med. & Biol. Eng. & Comp.*, 1979, 17, 641–646.

*Primary Examiner*—Lee S. Cohen
*Attorney, Agent, or Firm*—Karl F. Ross; Herbert Dubno

[57] ABSTRACT

An electrode arrangement for bioelectric signals, especially for EKG measurements comprises at least one electrode element in which the material in contact with the skin includes a p-n semi-conductor. Preferably the test electrode and a reference or neutral electrode are joined in a single unit in relatively close proximity.

6 Claims, 13 Drawing Figures

ELECTRODE FOR DETECTING BIOELECTRICAL SIGNALS

CROSS REFERENCE TO RELATED APPLICATION

This application is a continuation in part of Ser. No. 142,741 filed Apr. 22, 1980 now U.S. Pat. No. 4,375,219.

FIELD OF THE INVENTION

My present invention relates to electrodes for detecting or for the pickup of bioelectrical signals and, more particularly, to electrode assemblies adapted to determine bioelectrical conditions, especially in association with an apparatus for evaluating and/or plotting such signals as, for example, in EKG evaluations.

BACKGROUND OF THE INVENTION

In EKG analyses of the heart condition of a patient and for various other bioelectrical purposes, it is important as a diagnostic tool and as a measure of these conditions during surgery or recovery of a patient, to tap bioelectrical signals from the human body and evaluate or plot these signals as a function of time.

In EKG measurements, for example, potential differences longitudinally of the cardiac muscle fibers are analyzed. In the recording of the EKG, the electrical potential is registered as a function of time over a succession of heart beat signals between spaced-apart locations on the surface of the body of the patient by electrodes in contact with the skin.

So that these potentials may be detected at the surface of the skin, the electrodes are usually adhered to the skin and, to eliminate the effect of a superficial skin resistance, an electrode gel is applied between the skin and the electrode.

This gel is a conductive material which causes problems. For example, upon removal of the electrode, residues of the gel are left on the skin and must be removed.

Furthermore, the electrodes are connected by cables with a heart-frequency meter and usually must be spaced as far apart as possible, generally between 6 to 14 cm, so that bipolar effects at the skin surface do not detrimentally affect the potentials which are to be monitored by the EKG.

It has also been proposed (see, for example, the German patent document—open application—Offenlegungsschrift—DE-OS No. 1,566,162) to create an unpolarizable condition at the electrode by inserting between the electrode material and the skin a porous paper disk permeated with silver chloride. This system has the disadvantage that such additional elements must be handled by the EKG machine operator or technician.

German Patent document No. 27 42 058 discloses a double electrode arrangement in which the electrode bodies are mounted on a common insulating support. In this arrangement the skin-contact resistance reduces the level of the bioelectric signal which is to be monitored and, as a result a conductive gel must be applied.

Furthermore the spacing between the electrodes must be relatively large if interference is to be avoided because of the conductive gel.

OBJECTS OF THE INVENTION

It is the principal object of the present invention to provide an electrode assembly for EKG and other bioelectrical purposes, which can operate without an electrode gel or other contact element such as the disk mentioned previously, and yet can draw from the body, artifact-free bioelectrical signals without the disadvantages enumerated previously.

Yet another object of this invention is to provide an electrode system for the purpose described which is more reliable and more easily handled than earlier systems, which does not leave residues on the skin, and which affords fully reproducible results for a variety of applications.

It is still another object of this invention to provide an electrode assembly which permits the electrode elements, i.e. the test or input electrode or electrodes and a neutral or reference electrode, or two test or measurement electrodes and a reference or neutral electrode, to be disposed in closer proximity to one another while nevertheless affording precise values for the heart-frequency meter so that these values or signals can be evaluated without difficulty and without error.

A further object of this invention is to provide an improved EKG electrode unit which includes all of the electrodes for monitoring cardiac function and which can be applied to the patient elsewhere than in the chest region, especially for monitoring cardiac activity during chest surgery or other manipulations of the patient which limit access to the chest regions in the vicinity of the heart.

Yet another object of the invention is to provide an electrode unit which advances the principles set forth in my above-mentioned co-pending application.

SUMMARY OF THE INVENTION

These objects are attained, in accordance with the present invention, in an electrode assembly which is provided with at least one p-n semiconductor transition in the electrode material (i.e. a transition region between p-type and n-type materials). More specifically, the electrode of the present invention comprises an insulating body formed with a plurality of electrode members connectable to a circuit for evaluating, analyzing, recording or registering the signals from the electrode element, the electrode material which includes the p-n transition mentioned previously.

According to a feature of the invention, the electrode element includes a semiconductor element which forms with the p-n transition. The electrode material and a major component of the electrode material can consist of a noble metal alloy while minor components include at least one element from the group of ferrous metals, at least one semiconductor element and graphite.

More specifically, the electrode material preferably comprises 52 to 62% by weight of the noble metal, 3 to 6% by weight of the semiconductor element, about 3% by weight graphite, from trace amounts to up to 2% by weight of the ferrous-group metal, with the balance (to 100%) being conductive alloy-forming elements.

The electrode material as defined above can be shaped into round, polygonal or oval plates or disks by pressing, casting or like shaping methods used in the metallurgical arts. The reference to about 3% graphite is intended to mean 3%±0.7 and the trace amounts of the iron group metal can be present in as little as 0.001% by weight.

Each of the small p-n junction electrodes of the invention thus functions as a diode, the diodes being poled so as to be conductive in the same direction, e.g. away from the skin. If at least contact surfaces of the electrodes are formed from the aforementioned materials of high electrical conductivity, the two elements can be disposed in extremely close proximity (with a maximum spacing of 4 to 10 mm) without interference and with the ability to derive respective bioelectric signals. Thus the electrode assembly of the invention can be as small as an ordinary wristwatch and yet provide highly accurate readings.

Each electrode with a p-n junction according to the invention thus functions as a quasiactive electrode providing a sharp separation between the bioelectric signals and hence a higher level of output signals free from noise.

It has been found, further, that best results are obtained when the sides of the plates which are to rest against the skin are laterally unconfined. Furthermore, according to another feature of the invention, these sides are convex in the direction of the skin for one or both of the plates or disks of the assembly.

Furthermore, the side of the plates or electrode which rests against the skin can be formed with a conductivity-improving material or means, e.g. in the form of spaced-apart protuberances, a layer of highly conductive material, both such protuberances and the layer, or the like.

The plates or disks can have a mutual spacing which is approximately equal to the plate length or diameter (e.g. 4 to 5 mm) and can be completely or partly embedded in insulating material such as a nonconductive synthetic resin. In this case, the surfaces of the plates or disks which are to contact the skin should be coplanar with one another, i.e. flush, while the insulating material is flexible and/or the disks or plates are elastically mounted in the insulating material.

It has been found to be advantageous, moreover, to mount the disks or plates so that they are tiltable, rotatable or pivotable in the insulating material thereby accommodating their orientation to the skin contour to which the assembly is applied.

Furthermore, a neutral or reference electrode, (preferably of conductive material rather than a semiconductor or p-n junction) can be embedded in the insulating body. The neutral electrode can be a ring of circular or rectangular or other closed configuration.

The assembly can be fixedly or releasably mounted, e.g. plugged or screwed, in a support capable of applying and retaining the assembly against a portion of the body, e.g. an armband, wristband, strap or the like and the support may in turn be provided with the heart-frequency meter or can be connected readily thereto.

Each of the two electrodes of the assembly can have a contact element, for example, a contact pin, sleeve, wire, plug or jack, cooperating with a counter or complementary element which is connected to the digital circuitry of a high frequency meter.

According to a further aspect of the invention, each electrode element of the assembly is associated with an insulating layer and/or between the electrodes an insulating material is provided as a partition which can be cast between the electrodes. The electrodes, moreover, instead of having a disk or plate configuration, can be formed as rings, halfrings or curved members.

When the electrodes are constituted as rings a rigid or elastic insulation can be provided between, i.e. the electrodes can be secured together concentrically or co-axially by casting the insulating material between and/or around them.

In an alternative construction, one of the electrodes can be formed as a pin, plate or disk while the other electrode is disposed partly or completely around the first as a ring or partially circular electrode.

The electrodes or each electrode of the assembly can be protected from contact with water by a surrounding elastic sleeve which can extend between the outer electrode and a housing.

In yet another feature of the invention, the electrodes can be applied to or incorporated in an insulating band or strip or can be disposed in a common support at the vertices of a geometric figure such as a regular polygon.

The contact pins of the electrode can be screwed into or onto an electrode body or soldered or pressed to this body and/or cemented onto or into the body, e.g. with a conductive adhesive.

The electrode assembly can be associated with, i.e. can incorporate a function-controlling means such as a lamp, an acoustic or sound producing transducer or the like associated with at least one electrode and signaling the proper or improper functioning thereof.

I have also found it to be advantageous to provide a plurality of pin-type electrodes (between two to four are preferred) in an array angularly equal spaced about the central electrode which can be formed as a plate or disk. The housing of the assembly can also be provided in accordance with the present invention with a clock or like system for time measurement, e.g. with a stopwatch or alarm mechanism or circuit.

From the foregoing it will be apparent that the electrode assembly of the present invention provides an effective nullification of the detrimental influences of the skin resistance in a manner which could not be obtained with conventional electrodes even when electrode gels were used.

According to the invention as described, two electrodes (measurement or input electrodes) and the neutral or reference electrode can be disposed in close proximity with measurement results which nevertheless are at least as precise as the electrodes heretofore used for EKG measurements in spite of the many times greater spacing employed with the conventional electrodes.

This, of course, is what makes it possible to embed two electrodes with a minimum distance between them in a common body of insulating material so that both electrodes form a unit and that this unit (electrode set and/or dualelectrode) can be applied (adhered) directly to the skin.

To nullify any adhered effect of the skin resistance to the greatest possible extent, this electrode set can be applied to a correspondingly selected portion of the body and/or the extremities.

This advantage, gained because the spacing between the effective electrode is minimized, is especially significant when the electrode assembly is used during surgery or operations otherwise affecting the chest region.

In such cases, there is seldom enough place to provide the electrodes on the skin in the region of the heart. The electrode set or assembly can then be provided on the underarm or the upper leg portions of the patient without introducing into the monitored circuitry values which might detrimentally affect the results, i.e. without giving results which are less precise than those obtained with conventional widely spaced electrodes.

With the electrodes and electrode assemblies of the present invention, moreover, I find that oxidation is eliminated as a problem. It is well known that conventional electrodes are readily oxidized and are rapidly rendered unusable. They either must be cleaned in a time consuming manner or discarded.

BRIEF DESCRIPTION OF THE DRAWING

The above and other objects, features and advantages of the present invention will become more rapidly apparent from the following description, reference being made to the accompanying drawing in which.

SPECIFIC DESCRIPTION

Figure 1:
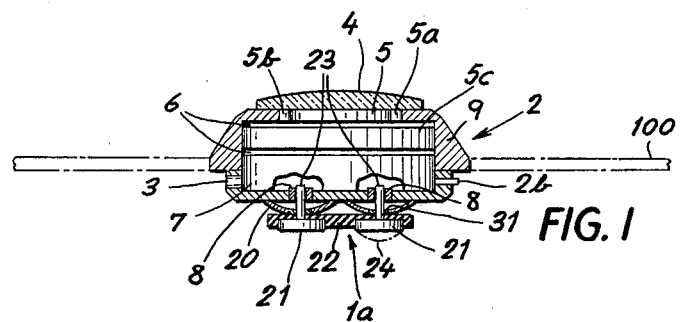
FIG. 1 is an elevational view partly broken away and partly in section, of an electrode assembly or set in accordance with the principles of the present invention.

The heart-frequency measuring assembly shown in FIG. 1 comprises a housing 2 which can be similar to a wristwatch housing or case and which contains the electrodes in an electrode set or a plurality of such electrode sets, which can be connected by cables, contact pins or the like to a conventional recording, evaluation or registration circuit e.g. the electronics of a conventional EKG machine.

The housing 2 can be formed with a miniature digital electronic circuit with low power draw for the digital measurement and display of the heart frequency. It can, for example, be provided with a high pass resonance amplifier to suppress the detection and display of movement artifacts and perturbations.

The housing 2 can be provided, for example, with a metallic armband 100, shown in dot-dash lines so that it can be applied in the region of the wrist of the patient in a manner analogous to a wristwatch. The armband 100 and/or the housing 2 can form the neutral or reference electrode.

The digital circuitry can include a digital display of the LCD type providing a numerical indication of the frequency. The digital circuit can also include an alarm to alert the wearer or the physician to the passage of the measured frequency above or below respective thresholds representing dangerously high or dangerously low pulse rates; preferably an acoustic signal is generated in this case.

Heart-frequency detection and pulse-indicating circuits of this type are described, for example, in German Patent Document—Open Application Offenlegungsschrift DE-OS No. 27 17 747.

The assembly shown in FIG. 1 has a watch-face window or crystal 4 which covers the space 5 provided with the optical display and the housing also comprises a portion 6 adapted to receive the measuring circuitry in a plurality of planes and a battery of the miniature type for energizing this circuitry.

The battery can be received in the portion 7 which can also include contacts and/or switches or controls for setting the upper and lower threshold frequency and for receiving the single generator for the alarm and contacts for the electrodes.

In the embodiment illustrated an electrode set 1a is provided on the underside of the housing 2.

The electrode set 1a comprises two electrodes 21 having the composition previously set forth in accordance with the present invention and disposed with a minimum spacing from one another.

These electrodes are held in place with the desired continuation by an insulating material or body 22 which can be a disk, plate or of another configuration or contour.

Contact pins 23 are secured to the electrodes 21 and can be fitted into contact sleeves 8 which are advantageously provided in the housing portion 7 as shown in FIG. 1. These sleeves are provided in the bottom of the housing and are so arranged that the pins can slide into and out of these sleeves but are retained against falling completely out of them. Springs 20 of the disk-type can yieldably bias the electrodes 21 outwardly while holding them against loss from the assembly.

The springs 20 press the electrodes firmly against the skin when the unit is applied to an extremity of the patient. While the springs can be composed of rubber or synthetic resin insulating disks of the Belleville type, they can also be metallic, in which case insulating brushes 31 are interposed between the springs 20 and the pins 23.

When the housing is affixed to the wrist of the patient, the outer surfaces of the electrode plates or disks are applied firmly against the skin and deliver signals to the heart-frequency meter circuit which provides the display.

It has been found to be advantageous to allow the tipping or tilting of the electrode set 1a without interfering with the contact between the pins 23 and the contact sleeves 8. This can be assured by slightly increasing the clearance between the sleeve and the pin. The tilting degree of mobility further improves the contact between the electrode and the skin.

Convex surfaces can be provided on the electrodes as has been represented at 24 in FIG. 1.

The skin-contacting surfaces of the electrode 21 should project sufficiently from the insulating material 22 that the latter does not hinder effective contact of the electrodes with the skin.

It is also important to ensure that no short circuit or leakage current can pass between the electrodes and thus an insulating barrier can be cast between them which is intended to reach to the skin. The electrodes, except for the contact surfaces, can also be sheathed wholly or partly in the insulating material.

The housing 2 is also provided with contact sleeves 3 enabling the cable connection between the electrodes and a remote circuit, e.g. an EKG machine, for use especially when the electrodes are applied to other body portions. In place of the contact sleeves 3, the housing 2 can have openings affording access to connecting terminals in the interior thereof.

The electrodes 21 can have various configurations as illustrated, for example, in FIGS. 3 and 6-13. In general, the electrode material will consist about of 52 to 62% by weight of a noble metal, 3 to 6% by weight of a semiconductor element, 2 to about 3% by weight graphite, and 0.5% to about 2% by weight of an iron group metal, the balance being conductive alloy-forming elements selected from the group of aluminum, copper and mercury.

The noble metals which are used in accordance with the invention are gold, silver, mercury, rhenium and the platinum group metals selected from ruthenium, rhodium, palladium, osmium, iridium and platinum. Two or more of these noble metals can be used in the noble metal component.

The iron group metals which are used in accordance with the present invention are cobalt, iron and nickel.

The semiconductor elements are selenium, tellurium, germanium and silicon.

The conductive alloy-forming elements can be any metals having good conductivity, preferably copper although aluminum can also be used.

The conductive alloy-forming element can be replaced by mercury, in which case the mercury can be an alloy former such that the alloy is an amalgam, assuming the mercury is not present in place of the other noble metals which have been listed. Typical alloys which are incorporated in the electrode in accordance with the present invention are mercury-gold, mercury-silver and mercury-copper alloys.

The following examples are illustrative of the preferred compositions of the present invention for the electrodes:

EXAMPLE I

| 1. Silver | 56 | parts by weight |
| 2. Copper | 34 | " |
| 3. Iron | 2 | " |
| 4. Germanium | 5 | " |
| 5. Graphite | 3 | " |

EXAMPLE II

| 1. Gold | 14 | parts by weight |
| 2. Mercury | 77 | " |
| 3. Iron | 2 | " |
| 4. Silicon | 4 | " |
| 5. Graphite | 3 | " |

EXAMPLE III

| 1. Platinum | 10 | parts by weight |
| 2. Mercury | 81 | " |
| 3. Iron | 1 | " |
| 4. Silicon | 5 | " |
| 5. Graphite | 3 | " |

EXAMPLE IV

| 1. Silver | 11 | parts by weight |
| 2. Mercury | 81 | " |
| 3. Nickel | 1 | " |
| 4. Silicon | 4 | " |
| 5. Graphite | 3 | " |

The electrode materials can be pressed from particles of the amalgam and other elements as recited by conventional powder metallurgy techniques, or can be formed by casting.

Figures 2, 3, 4:
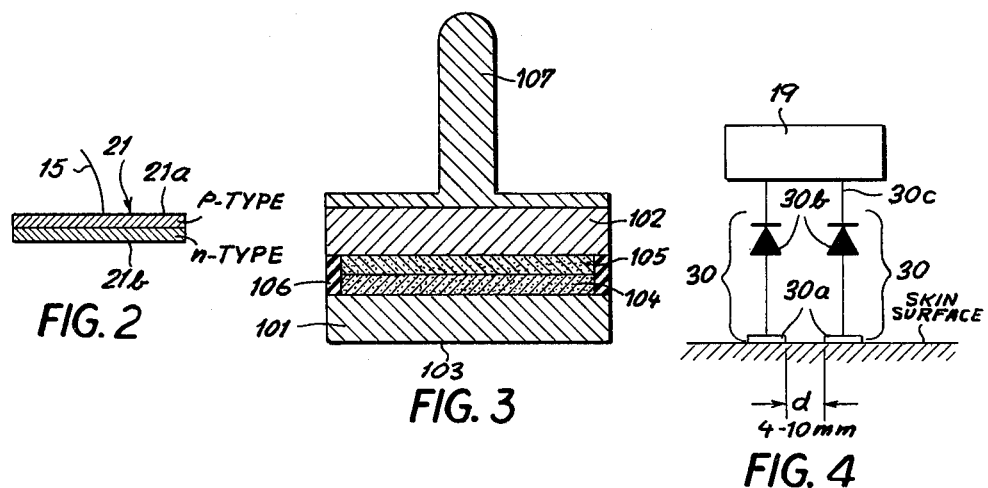
FIGS. 2 and 3 are cross sectional views through respective embodiments of electrodes according to the invention.
FIG. 4 is a diagram illustrative of the invention.

In FIG. 2 I have shown a simple electrode 21 which comprises a body of conductive material in accordance with Examples I through IV, the upper portion of which may be doped with a semiconductor element to form a p-type semiconductor 21a while the lower part is doped with a semiconductor element to form the n-type semiconductor 21b. The underside of this electrode, which is in the form of a disk, is applied to the skin and can have a conductivity-increasing layer of a noble metal, while the opposite side has a conductor 15 affixed to it.

In FIG. 3, I show another embodiment of an electrode which can be used for the electrode 21 or 30 as previously or subsequently described.

Two plates 101 and 102 of conductive material (see one of the previous examples) are doped in limited regions 104, 105 with p-type and n-type semiconductor, respectively, thereby forming the p-n junction which is surrounded by an insulating sleeve 106. Surface 103 forms the contact face of this electrode while a pin 107 is affixed to the opposite face to constitute the lead or connection corresponding to the pins 23 previously described.

The principle of operation of the double electrode assembly is illustrated in FIG. 4. Each electrode 30 has a highly conductive contact surface 30a, a p-n junction 30b and a conductor 30c which is connected to a monitoring circuit, e.g. the circuit 19 described below.

Each electrode 30 thus functions as a diode as shown in FIG. 4 and the diodes are poled in the same direction thereby automatically insulating them from one another.

The electrodes 21, 30 should have relatively small dimensions and a typical set of such dimensions can be a height or thickness of 1.5 to 3 mm and a diameter of 4 to 5 mm.

Figure 5:
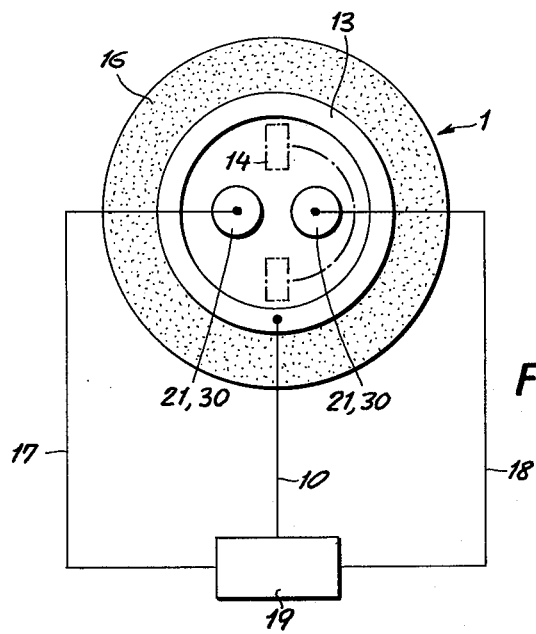
FIG. 5 is a diagram illustrating a system using two measurement electrodes.
Figure 6:
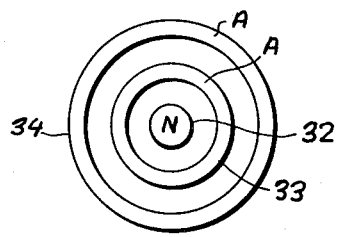
FIGS. 6-13 are diagrams showing various orientations and arrangements of electrodes in assembly falling within the purview of the instant invention.

A particularly advantageous disposition of the electrodes in the assembly of the present invention has been shown in FIG. 5. It will be seen from this FIGURE that the two measuring or input electrodes 21 or 30 are disposed in closely spaced relationship diametrically on opposite sides of the axis of the assembly of FIG. 1 and are connected by conductors represented at 17 and 18 to an input amplifier 19. The neutral or reference electrode ring 13 is connected by the conductor 10 to the amplifier as well.

The ring 13 can be fitted onto the assembly shown in FIG. 1 or dispensed with entirely when the band 100 or the housing 2 form the neutral electrode. Furthermore, in addition to the ring 13 (or in place thereof) a pair of rectangular strip-shaped electrodes 14 can be provided at diametrically opposite locations, the strips being connected electrically to one another as shown in FIG. 5.

The electrodes are all held in place vis-á-vis one another by the insulating material, e.g. 22, in which the electrodes are embedded or anchored. The contact ring 13 can be a metal ring, e.g. of copper, and apart from the circular or round configuration shown in FIG. 5, can have a polygonal or oval configuration if desired.

The contact side of the electrode assembly can also be provided with a synthetic resin adhesive ring 16 of conventional design. This ring is not essential to the invention and facilitates securing the assembly to the skin of the patient. Other means can be provided for this purpose e.g. in the form of adhesive tape or the like.

With the system of the present invention, I have found that it is possible to minimize or eliminate the bridging or shunt resistance of the skin with respect to the electrodes even when the electrodes are relatively close together as described. Naturally, when the resistance between the skin and the electrode surface is relatively high, the electrode spacing must be proportionately greater to eliminate the shunting effect. Thus it is some times desirable, within the overall concept of the present invention, to allow a somewhat greater spacing between the electrodes than has been indicated in FIG. 5. This can be achieved with a system such as has been shown in FIG. 6 in which the neutral electrode 32 is disposed at the center of a pair of concentric circles formed by the active electrodes 33 and 34 which are rings.

The contact areas of the electrodes can be equal, in which cases the rings will be of different thickness, although it is also possible to make the areas different.

If the contact surface of the electrode 32 is about 20 mm$^2$ (19.63 mm$^2$ in the case of a diameter of 5 mm) the rings should have the same or larger areas.

It is also possible to utilize one of the rings as a neutral electrode and the other ring and the center electrode as the active electrode. In the drawing the preferred arrangement of the neutral and active electrodes has been designated by the letter N for neutral and A for active.

Figure 7:
Figure 8:
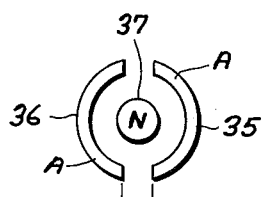

Of course, while concentric electrodes are preferred, either if one or more of the electrodes are annular or are disposed in equispaced relationship about a center or an axis, a linear array of the electrodes is also possible as is shown in FIG. 7. The neutral electrode N can also be the center electrode and will then be flanked by two active electrodes. In this case, the active electrodes 35 and 36 are arcuate and partially circular so that together they define opposite sides of a flattened circle e.g. an ellipse, about the neutral electrode 37 located at the center. The spacing 38 between the electrodes 35 and 36 should be 4 to 5 mm or more. Naturally, even in this embodiment, one of the arcuate electrodes can be formed as the neutral electrode and the central electrode as an active electrode.

Figure 9:
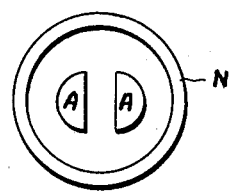
Figure 10:
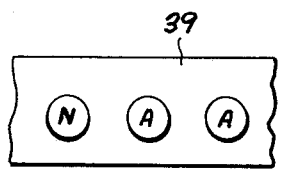

Still another particularly advantageous configuration has been shown in FIG. 9 in which the two active electrodes are of semicircular configuration or some other configuration, e.g. square or rectangular, while the neutral electrode N forms a ring around them.

The individual electrodes, N, A, A (FIG. 10) can be applied to an adhesive strip 39 with appropriate spacing. These electrodes need not be in a linear array. For example, they can be disposed at the vertices of a triangle.

Figure 11:
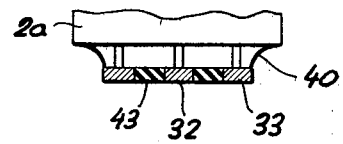
Figure 12:
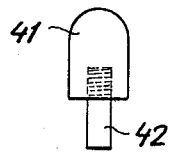

FIG. 11 shows an arrangement in which the housing 2a, which can be otherwise similar to the housing 2 of FIG. 1, carries an outer electrode ring 33 to which an elastic sleeve 40 is secured, this sleeve 40 bridging the gap between the ring and the housing 2a to enable relatively flexible movement of the electrode while sealing the space between the effective surface and the housing against moisture. Between the electrode ring 33 and the central electrode 32, the insulating material 43 is provided. This material can also be flexible.

The electrodes, as in the embodiment of FIG. 1, can have contact pins which extend into the housing. In an alternative construction, the electrodes 21 can be replaced by outwardly convex members 41 which are threaded onto the pins 42. The pins 42 can be tubular and designed to engage an external thread on the electrode members 41 in a variant of this concept shown in FIG. 12.

It has been found to be advantageous, moreover, to maintain the entire housing 2 at a predetermined temperature, especially when the device shown in FIG. 1 is to be used in cold regions. In this case, the housing is provided with a heating coil together with a thermostat to maintain the temperature. Inner and outer layers of thermal insulation can also be provided on the housing 2 or 2a.

The display 5 can include a glow lamp 5a or an electro-acoustic transducer 5b to signal the functioning of the device and, or, a sufficient charge of the battery when, for example, the button 2b is pressed.

Figure 13:
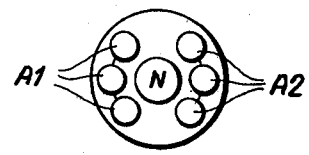

The electrode configuration shown in FIG. 13 comprises six electrode pins forming the active electrodes A1 and A2 are of the configuration of member 41 previously described, the three pins of each electrode being connected together. The neutral electrode N can correspond to the electrodes 32 and 37 previously described.

The housing is provided with a stopwatch or wrist alarm mechanism 5c as previously described.

What is claimed is:

1. An electric assembly for skin-contacting bioelectrical purposes, comprising:
   a support;
   a pair of electrodes mounted on and insulated from one another by said support, said electrodes having side-by-side contact surfaces adapted to rest directly against the skin, terminals enabling electrical connection to the respective electrodes and means forming a respective p-n junction poled in the same direction as the p-n junction of the other electrode with respect to the skin between each contact surface and the respective terminal, each such means including a plate of p-conductive semiconductive material lying against a plate of n-conductive semiconductive material, said plates being parallel to the respective contact surface; and
   means for connecting said terminals of said electrodes to a device for monitoring bioelectric signals traversing said p-n junctions from the skin.

2. The assembly defined in claim 1 wherein said electrodes are formed predominantly and apart from the respective p-n junctions of an alloy consisting in major parts of a noble metal and in minor parts of at least one iron-group metal, at least one semiconductor element, and graphite.

3. The assembly defined in claim 2 wherein each of said electrodes has a body consisting essentially of 52 to 62% by weight of at least one noble metal, 3 to 6% by weight of at least one semiconductor element, about 2 to about 3% by weight graphite and from trace amounts to about 2% by weight of an iron-group metal, the balance being conductive alloy forming elements.

4. The assembly defined in claim 1 wherein said support is provided with a wristband to enable the same to be fixed to the wrist of a person, said support being provided with a heartbeat frequency meter connected to said electrodes by said connecting means.

5. The assembly defined in claim 4 wherein said support is composed at least in part of elastically deformable material yieldable to permit resilient displacement of said electrodes.

6. The assembly defined in claim 4, further comprising spring means between said support and said electrodes for yieldably retaining said contact surfaces against the skin.

* * * * *